United States Patent [19]

Yarovesky et al.

[11] Patent Number: 5,482,459
[45] Date of Patent: Jan. 9, 1996

[54] POSTERIOR TOOTH SHADE GUIDE AND METHOD OF SELECTING CHARACTERIZATION FOR A TOOTH PROSTHESIS

[75] Inventors: Uriel Yarovesky, Woodland Hills; Daniel Materdomini, Topanga Canyon, Calif.

[73] Assignee: Dental Illusions, Woodland Hills, Calif.

[21] Appl. No.: 297,251

[22] Filed: Aug. 26, 1994

Related U.S. Application Data

[63] Continuation-in-part of Ser. No. 22,420, May 4, 1994, Pat. No. Des. 357,321, and Ser. No. 22,409, May 4, 1994, Pat. No. Des. 357,320.

[51] Int. Cl.$^6$ .............................. A61C 19/10; A61C 5/00
[52] U.S. Cl. .............................................. 433/26; 433/215
[58] Field of Search ...................... 433/26, 203.1, 433/215

[56] References Cited

U.S. PATENT DOCUMENTS

| | | | |
|---|---|---|---|
| 4,207,678 | 6/1980 | Jeannette | 433/203.1 |
| 4,657,399 | 4/1987 | Hall | 433/26 |
| 4,802,850 | 2/1989 | Boon | 433/26 |
| 4,828,117 | 5/1989 | Panzera et al. | 433/203.1 |
| 5,004,417 | 4/1991 | Giaramita | 433/26 |
| 5,114,340 | 5/1992 | Hahn | 433/26 |
| 5,240,414 | 8/1993 | Thompson | 433/26 |

*Primary Examiner*—Cary E. O'Connor
*Attorney, Agent, or Firm*—Kelly, Bauersfeld & Lowry

[57] ABSTRACT

A posterior tooth shade guide includes a plurality of posterior tooth samples each positionable upon a posterior tooth holder and bearing differing tooth characteristics. Several of the tooth samples have differing white stain characteristics, others have differing brown stain characteristics, and still others have differing incisal layer colors. Another set have differing percentages of the incisal that covers the body of the tooth prosthesis. A selector ring is provided to permit the selection of a specific brown stain color. Utilizing the posterior tooth shade guide, a dentist and the laboratory may utilize a method for selecting characterizations of a tooth prosthesis wherein the posterior tooth samples are utilized to select: brown stain characteristics, white stain characteristics, incisal layer color, and the percentage of the incisal that covers the body of the tooth prosthesis. This information, coupled with the specific stain color and the general tooth color selected from a shade guide and, optionally, a drawing prepared to show additional tooth characterization features, permits the dentist to relay to the laboratory an accurate representation of the tooth prosthesis to be manufactured.

30 Claims, 4 Drawing Sheets

LIGHT INCISAL

DARK INCISAL

WHITE INCISAL

YELLOW INCISAL

CHALKY WHITE INCISAL

CHALKY WHITE GRAY INCISAL

GRAY INCISAL

POSTERIOR TOOTH SHADE GUIDE AND METHOD OF SELECTING CHARACTERIZATION FOR A TOOTH PROSTHESIS

RELATED APPLICATIONS

This is a continuation-in-part of U.S. patent application Ser. No. 29/022,420, filed May 4, 1994 and entitled POSTERIOR TOOTH HOLDER FOR DENTAL STAIN CHARACTERIZATION GUIDE, now U.S. Pat. No. D357,321 and U.S. patent application Ser. No. 29/022,409, filed May 4, 1994 and entitled DENTAL CHARACTERIZATION GUIDE, now U.S. Pat. No. D357,320.

BACKGROUND OF THE INVENTION

This invention relates generally to the field of dentistry. More specifically, the present invention relates to a posterior tooth shade guide and a method of selecting characterization for a tooth prosthesis.

Accurate communication between dentists and laboratories that manufacture tooth prostheses has been a subject of continuous concern as technology progresses. When instructing the laboratory to construct a tooth prosthesis, it is desirable to manufacture the prosthesis in such a manner that it is virtually indistinguishable from the surrounding natural teeth.

Many manufacturers of tooth prostheses provide performes samples of multi-color, multi-layer fabricated teeth as references for color. The dentist may communicate to the lab regarding the desired color of the tooth prosthesis utilizing a shade guide having a number of these fabricated teeth for reference. In this regard, the dentist typically holds a sample tooth against the mouth in an attempt to find the closest sample to the natural tooth.

Such dental shade guides typically include a number of anterior tooth-shaped and detailed samples that neither resembled posterior teeth nor have the descriptive details of posterior teeth. These anterior tooth samples are used by the dentists for both anterior and posterior tooth color matching.

The prior shade guides are inadequate for purposes of describing the unique characterizations that posterior teeth have and which are not usually found with anterior teeth. In particular, to manufacture a tooth prosthesis for a posterior tooth, characteristics such as the brown stain, the white stain, and the color of the incisal should be taken into account.

Accordingly, there has been a need for a posterior tooth shade guide and method of selecting characterization for a tooth prosthesis which can simply, yet effectively, facilitate accurate communication of the desired characteristics of a tooth prosthesis from the dentist to the laboratory. The present invention fulfills these needs and provides other related advantages.

SUMMARY OF THE INVENTION

The present invention resides in a novel posterior tooth shade guide and a related method, which permit a dentist to relay to the laboratory an accurate representation of a tooth prosthesis to be manufactured. The posterior tooth shade guide includes a plurality of posterior tooth samples each positionable upon a posterior tooth holder and bearing different tooth characteristics. Several of the tooth samples have differing white stain characteristics, others have differing brown stain characteristics, and still others have differing incisal layer colors. Another set has differing percentages of the incisal that covers the body of the tooth prosthesis. A selector ring is provided to permit the selection of a specific brown stain color.

Utilizing the posterior tooth shade guide, a dentist and the laboratory may utilize a method for selecting characterizations of a tooth prosthesis wherein the posterior tooth samples are utilized to select brown stain characteristics, white stain characteristics, incisal layer color, and the percentage of the incisal that covers the body of the tooth prosthesis. This information, coupled with the specific brown stain color and the general tooth color selected from a standard shade guide and, optionally, a drawing prepared to show additional tooth characterization features, permits the dentist to relay to the laboratory an accurate representation of the tooth prosthesis to be manufactured.

In a preferred form of the invention, the method for selecting characterizations for a tooth prosthesis begins with the step of selecting a general tooth color from a shade guide. Next, a brown stain characteristic is selected from an occlusal table. This step includes the step of selecting from a plurality of posterior tooth samples having differing brown stain characteristics. A white stain characteristic is then selected from the occlusal table. This is accomplished by selected the desired white stain characteristic from a plurality of posterior tooth samples having differing white stain characteristics. The incisal layer color is then selected as an occlusal overlay. This step includes the step of selecting the desired incisal layer color from a plurality of posterior tooth samples having differing incisal layer colors.

Next, a percentage of the incisal to cover a body of the tooth prosthesis is selected. This includes the step of selecting the percentage from a plurality of posterior tooth samples having differing percentages of the incisal that covers the body of the tooth prosthesis. The dentist may then select a specific brown stain color from, preferably, a selector ring having a plurality of sticks pivotally secured to a circular ring, wherein each stick bears a unique color stain relative to the other sticks secured to the ring.

To complete the process and to ensure that the laboratory is given an accurate representation of the tooth prosthesis to be manufactured, a drawing may be prepared to show additional tooth characterization features. In this regard, it is preferred that both occlusal and labial drawings are provided.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 1:
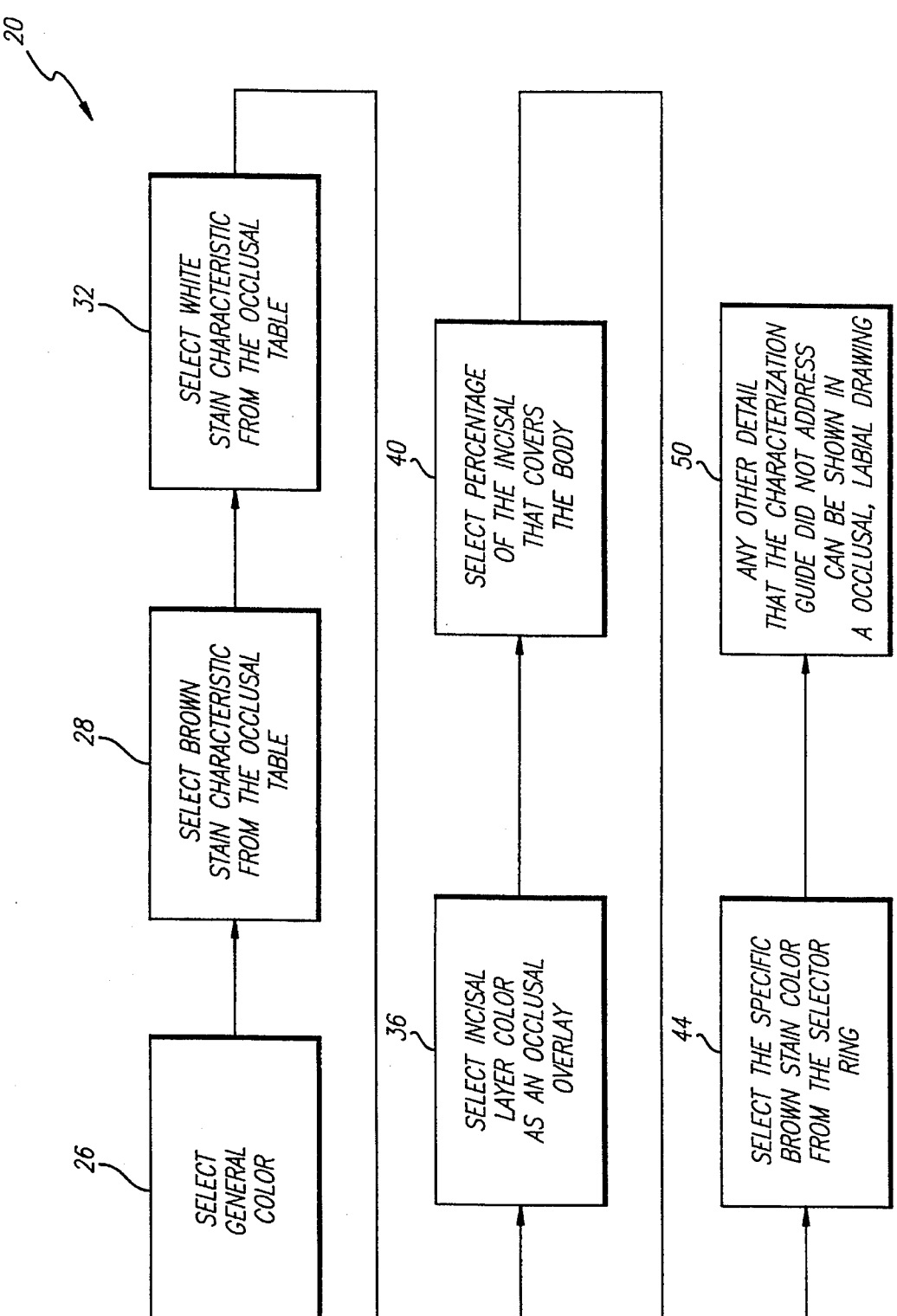
FIG. 1 is a flow chart illustrating the steps of the method of selecting characterizations for a tooth prosthesis in accordance with the present invention.
Figure 6:
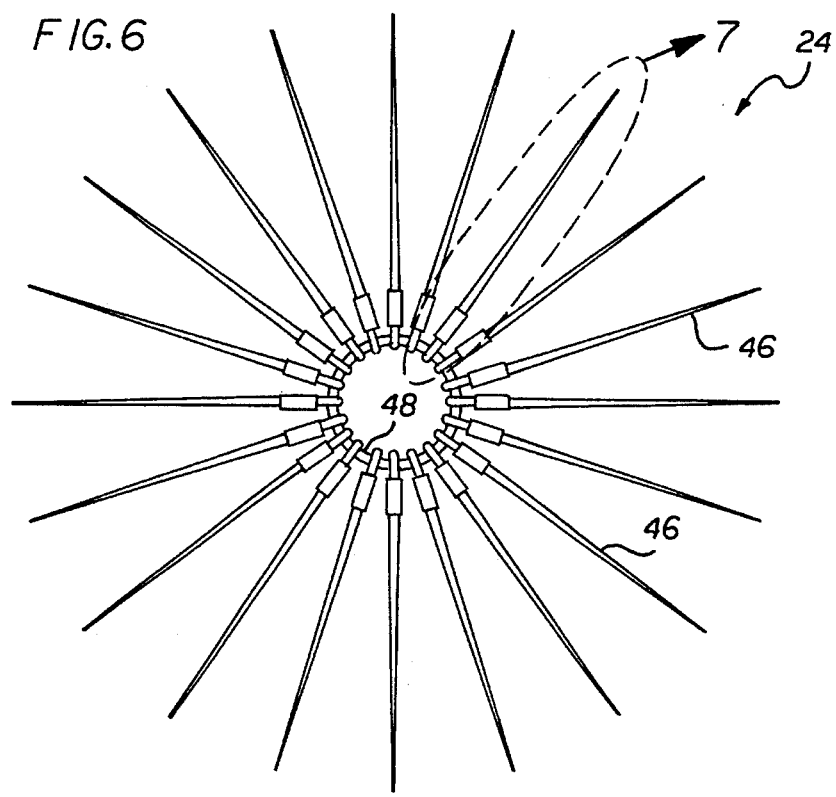
FIG. 6 is an elevational view of a dental stain guide comprising a multi-stain color selector ring.
Figure 7:
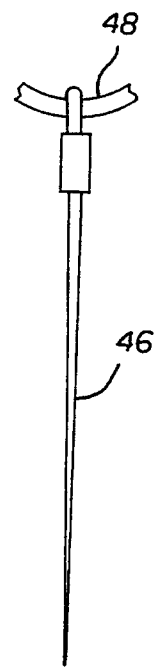
FIG. 7 is an enlarged partially fragmented view of the portion of the dental stain guide designated by the number 7 in FIG. 6.
Figure 9:
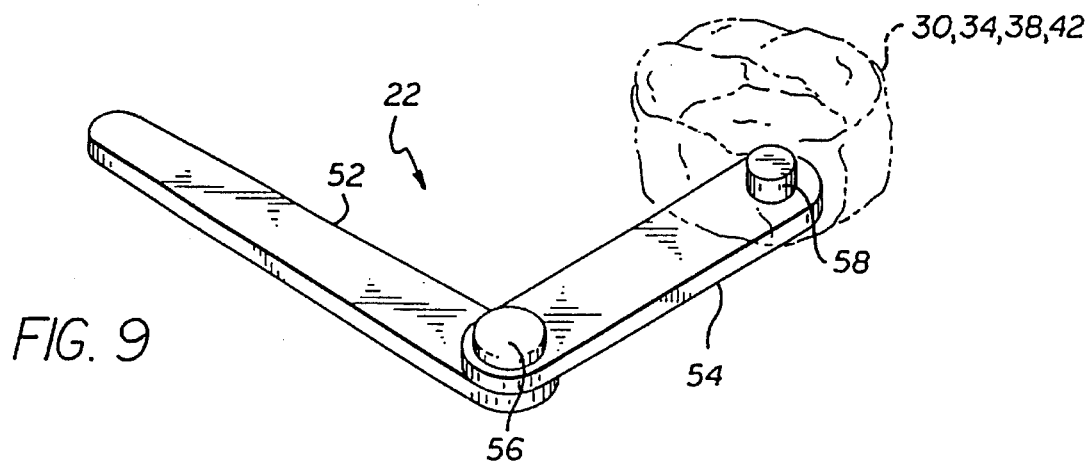
FIG. 9 is a perspective view of a posterior tooth holder for a dental stain characterization guide, wherein an exemplary posterior tooth sample is shown in phantom.
Figure 10:
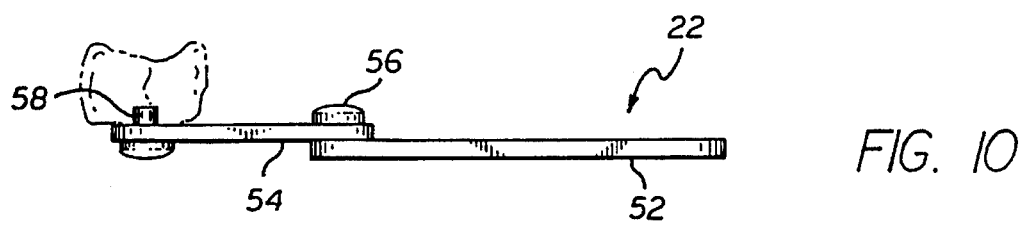
FIG. 10 is a front elevational view of the posterior tooth holder shown in FIG. 9.
Figure 11:
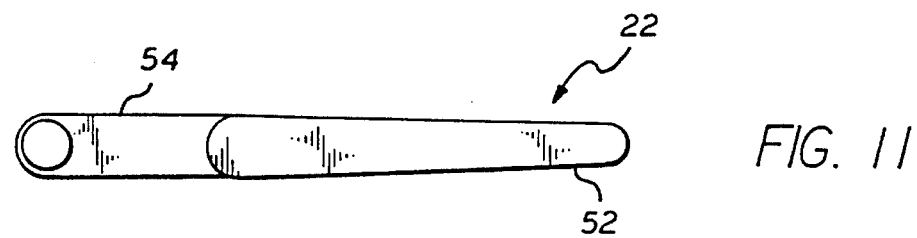
FIG. 11 is a bottom plan view of the posterior tooth holder of FIGS. 9 and 10.
Figure 12:
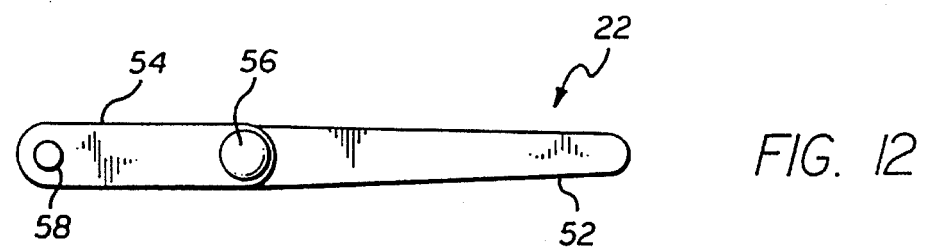
FIG. 12 is a top plan view of the posterior tooth holder of FIGS. 9–11.
Figure 13:
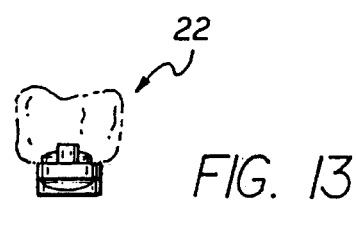
FIG. 13 is a left side elevational view of the posterior tooth holder of FIGS. 9–12.
Figure 14:
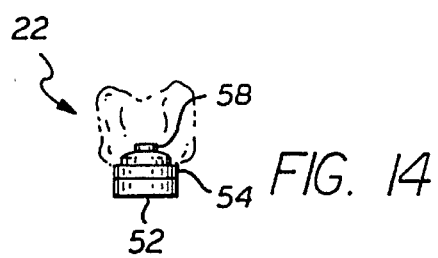
FIG. 14 is a right side elevational view of the posterior tooth holder of FIGS. 9–13.

As shown in the drawings for purposes of illustration, the present invention is concerned with a method of selecting characterizations for a tooth prosthesis, which method is generally designated in FIG. 1 by the reference number 20. The improved method 20 is practiced in connection with a posterior tooth shade guide which comprises a plurality of posterior tooth samples, to be discussed in detail below, a posterior tooth holder 22 (FIGS. 9–14), and a selector ring 24 (FIGS. 6 and 7). The posterior tooth shade guide and the method 20 of selecting characterizations for a tooth prosthesis, permit a dentist to relay to the laboratory an accurate representation of a tooth prosthesis to be manufactured.

In accordance with the present invention and with reference to FIG. 1, the method 20 for selecting characterizations for a tooth prosthesis begins with the step of selecting the general color of the tooth prosthesis, indicated by the block 26. Most any existing standard shade guide may be utilized for purposes of selecting the general color of the tooth prosthesis to be manufactured. In terms of industry standard nomenclature, the color chosen will be indicated as within the range from A1–A4, B1–B4, C1–C4, etc. Once one of the standard shades of an available shade guides is selected as being the tooth shade closest to the natural tooth, the dentist may then utilize the posterior tooth shade guide of the present invention to accurately select the most desirable characterizations for the tooth prosthesis.

Figures 2A, 2B, 2C, 2D:
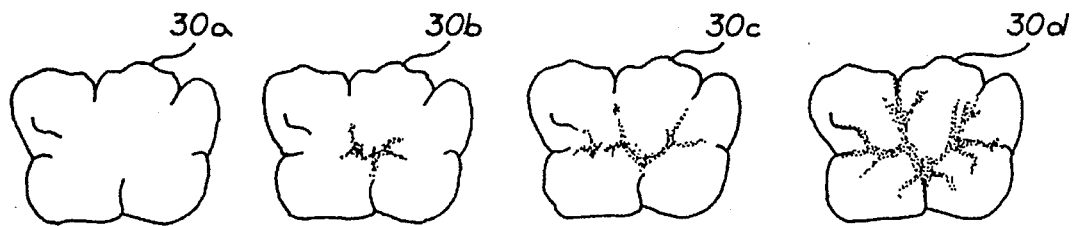
FIGS. 2A–2D are top plan views of several posterior tooth samples having varying degrees of brown stain.

The next step of method 20, indicated by block 28 of FIG. 1, is to select a brown stain characteristic from an occlusal table. In the preferred posterior tooth shade guide the occlusal table includes a plurality of posterior tooth samples having different characteristics. In the illustrated embodiment, a plurality of posterior tooth samples 30a–30d are provided which each have differing brown stain characteristics. FIG. 2A illustrates a tooth sample 30a having no brown stain, FIG. 2B illustrates a tooth sample 30b having a light brown stain, FIG. 2C illustrates a tooth sample 30c having a medium brown stain, and FIG. 2D illustrates a tooth sample 30d having a heavy brown stain. The dentist would select the brown stain to be applied to the tooth prosthesis from the tooth samples 30a–30d, and select the most appropriate brown stain characteristic for the tooth prosthesis. A shorthand notation for the brown stain of the tooth samples 30a–30d is BS1–BS4.

Figures 3A, 3B, 3C, 3D:
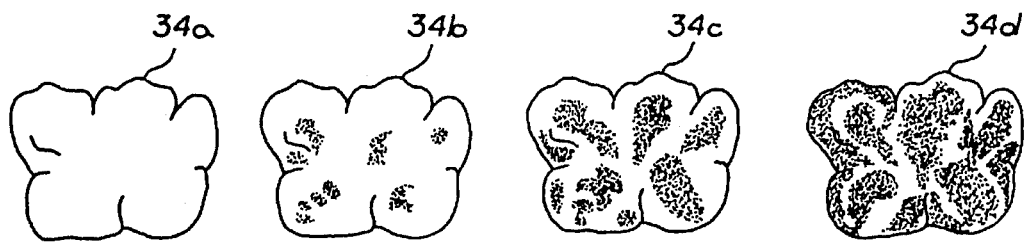
FIGS. 3A–3D are top plan views of several posterior tooth samples having varying degrees of white stain.

Next, as illustrated in block 32 of FIG. 1, a white stain characteristic for the tooth prosthesis is selected from the occlusal table. With reference to FIGS. 3A–3D, several posterior tooth samples 34a–34d are provided which have differing white stain characteristics. FIG. 3A shows a tooth sample 34a having no white stain, FIG. 3B shows a tooth sample 34b having a light white stain, FIG. 3C shows a tooth sample 34c having a medium white stain, and FIG. 3D shows a tooth sample 34d having a heavy white stain. The white stain shown on the samples 34a–34d is indicated through simple nomenclature such as W1–W4. As was the case when selecting the brown stain characteristic from the occlusal table, the dentist simply selects which of the tooth samples 34a–34d most accurately shows the white stain characteristic desired for the tooth prosthesis to be manufactured.

Figure 4A:
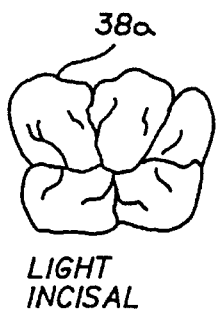
FIGS. 4A–4G are top plan views of several posterior tooth samples having varying incisal layer colors.
Figure 4B:
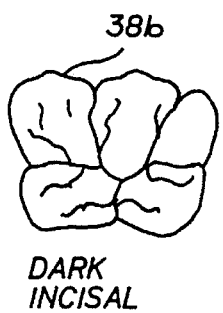
Figure 4C:
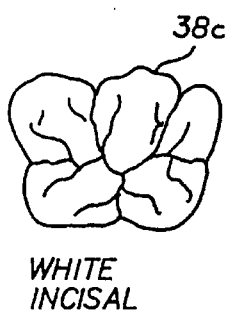
Figure 4D:
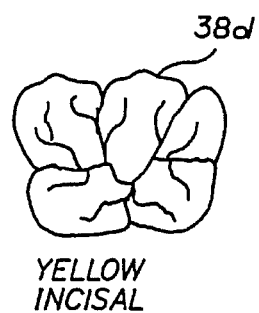
Figure 4E:
Figure 4F:
Figure 4G:
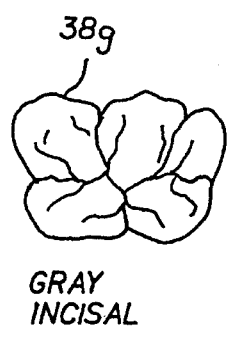

As indicated by the block 36 in FIG. 1, the next step is to select an incisal layer color as an occlusal overlay. Once again reference is made to a plurality of posterior tooth samples 38a–38g (FIG. 4) in order to select the desired incisal layer color. FIG. 4A illustrates a tooth sample 38a having a light incisal color, FIG. 4 B illustrates a tooth sample 38b having a dark incisal color, FIG. 4C illustrates a tooth sample 38c having a white incisal color, FIG. 4D illustrates a tooth sample 38d having a yellow incisal color, FIG. 4E illustrates a tooth sample 38e having a chalky white incisal color, FIG. 4F illustrates a tooth sample 38f having a chalky white grey incisal color, and FIG. 4G illustrates a tooth sample 38g having a grey incisal color. The typical shorthand notation for recording the selected incisal layer color may be Inc1–Inc7.

Figures 5A, 5B, 5C, 5D, 5E:
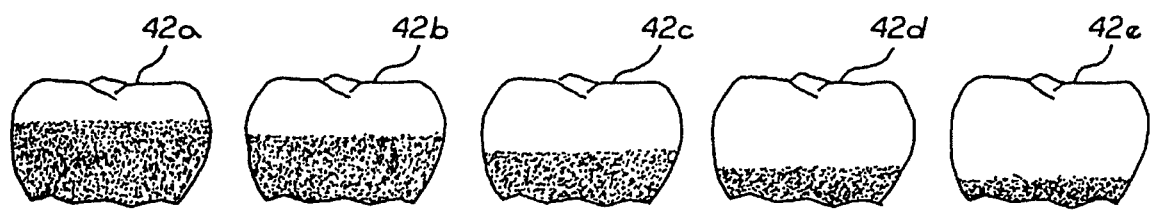
FIGS. 5A–5E are side elevational views of several posterior tooth samples having varying percentages of the incisal that covers the body of the tooth prosthesis.

Next, as indicated by the block 40 of FIG. 1, the percentage of the incisal to cover a body of the tooth prosthesis is selected. FIGS. 5A–5E show a plurality of posterior tooth samples 42a–42e which have differing percentages of the incisal that the covers the body of the tooth prosthesis. FIG. 5E shows a tooth sample 42a wherein twenty-five percent of the incisal covers the body of the tooth prosthesis. FIG. 5B illustrates a tooth sample 42b wherein thirty percent of the incisal covers the body of the tooth prosthesis. FIG. 5C shows a tooth sample 42c wherein fifty percent of the incisal covers the body of the tooth prosthesis. FIG. 5D shows a tooth sample 42d wherein seventy-five percent of the incisal covers the body of the tooth prosthesis. FIG. 5E shows a tooth sample 42e wherein ninety percent of the incisal covers the body of the tooth prosthesis. As in all of the cases noted above, the dentist selects from among these tooth samples 42a–42e to determine which most accurately reflects the characterization to be included in the tooth prosthesis to be manufactured.

Although the brown stain characterization has already been accomplished with reference to the tooth samples 30a–30d, it remains for the dentist to select the specific color of stain to be applied to the tooth prosthesis. This is accomplished, as shown in block 44, by utilizing the selector ring 24. The selector ring 24 includes a plurality of sticks 46 which are pivotally secured to a circular ring 48. Each stick 46 bears a unique brown stain color or other color relative to the other sticks secured to the ring 48. The sticks 46 are constructed to enable the dentist to select any one stick and place it in the mouth adjacent to the patient's natural teeth to permit the selection of the most appropriate brown stain color.

Figures 8A, 8B:
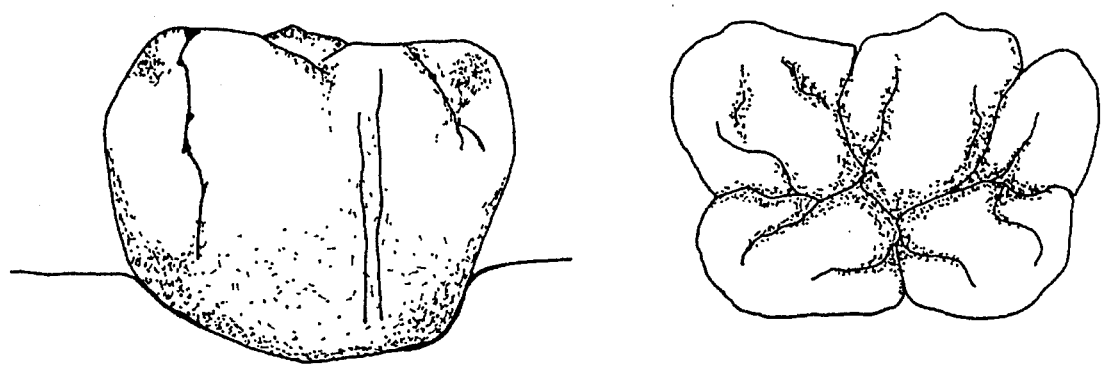
FIG. 8A is an exemplary labial drawing for a tooth prosthesis to show additional tooth characterization features.
FIG. 8B is an exemplary occlusal drawing of the tooth shown in FIG. 8A.

As a final step in the method 20, as illustrated in block 50 of FIG. 1, any other details that the characterization guide did not address can be shown in occlusal and labial drawings. Exemplary occlusal and labial drawings are illustrated in FIGS. 8A and 8B. Drawings such as these may be utilized to show the exact locations of sulcus stains and other unique features of the tooth prosthesis to be manufactured.

When utilizing the posterior tooth shade guide of the present invention, it is often desirable to place the tooth samples adjacent to the natural teeth to ensure accurate selection of the proper characteristics. For this purpose the posterior tooth holder 22 is provided to facilitate convenient placement of the tooth samples within the patient's mouth. The posterior tooth holder 22 includes a handle 52 and an arm 54 pivotable relative to the handle 52 by means of a connector 56. A mounting post 58 supported on the arm 54 opposite the connector 56 provides means for mounting a tooth sample thereon (see FIGS. 9–14).

From the foregoing it is to be appreciated that the posterior tooth shade guide of the present invention may be advantageously utilized by dentists and laboratory technicians alike to ensure more accurate communication regarding the characteristics of a tooth prosthesis to be manufactured. By way of example, a dentist may submit to a laboratory a request to manufacture a posterior tooth prosthesis with the designation B3, BS2.5, W3, Inc6, 50%, accompanied by labial and occlusal drawings showing additional tooth characterization features. The laboratory technician would then know, from the foregoing, that the general color of the tooth prosthesis would correspond to the B3 designation, the brown stain characteristic would fall between the light and medium brown stains shown in the tooth samples 30b and 30c, the white stain characteristic would be as shown in the tooth sample 36c, the incisal layer color would correspond to the chalky white grey incisal of the tooth sample 38f, and that the percentage of the incisal that covers the body of the tooth prosthesis will most closely approximate the tooth sample 42c (fifty percent). Of course, the particular stain color selected utilizing the selector ring 24 would also be communicated by the dentist, and utilized by the laboratory constructing the tooth prosthesis.

Although a particular embodiment of the invention has been described in detail for purposes of illustration, various modifications may be made without departing from the spirit and scope of the invention. For example, it will be understood that while the posterior tooth shade guide utilizes actual tooth samples for purposes of the comparisons and selections of the desired tooth prosthesis characteristics, the methods of the present invention may be practiced utilizing prints and disposable plastic representations of the anterior tooth characterization guide. Accordingly, the invention is not to be limited, except as by the appended claims.

We claim:

1. A method for selecting characterizations for a tooth prosthesis, comprising the steps of:
   selecting a general tooth color for the tooth prosthesis from a shade guide;
   selecting a brown stain characteristic for the tooth prosthesis from an occlusal table;
   selecting a white stain characteristic for the tooth prosthesis from the occlusal table; and
   selecting an incisal layer color for the tooth prosthesis as an occlusal overlay.

2. The method of claim 1, wherein the step of selecting a brown stain characteristic includes the step of selecting from a plurality of posterior tooth samples having differing brown stain characteristics.

3. The method of claim 2, including the step of selecting a specific stain color.

4. The method of claim 3, including the step of selecting the specific stain color from a selector ring.

5. The method of claim 1, wherein the step of selecting a white stain characteristic includes the step of selecting from a plurality of posterior tooth samples having differing white stain characteristics.

6. The method of claim 1, wherein the step of selecting an incisal layer color includes the step of selecting from a plurality of posterior tooth samples having differing incisal layer colors.

7. The method of claim 6, including the step of selecting a percentage of the incisal to cover a body of the tooth prosthesis.

8. The method of claim 7, wherein the step of selecting a percentage of the incisal to cover the body of the tooth prosthesis, includes the step of selecting from a plurality of posterior tooth samples having differing percentages of the incisal that covers the body of the tooth prosthesis.

9. The method of claim 1, including the step of preparing a drawing for the tooth prosthesis to show additional tooth characterization features.

10. The method of claim 9, wherein the step of preparing a drawing includes the steps of preparing both occlusal and labial drawings.

11. A method for selecting characterizations for a tooth prosthesis, comprising the steps of:
    selecting a brown stain characteristic for the tooth prosthesis from an occlusal table;
    selecting a white stain characteristic for the tooth prosthesis from the occlusal table; and
    selecting an incisal layer color for the tooth prosthesis as an occlusal overlay.

12. The method of claim 11, including the step of selecting a specific stain color.

13. The method of claim 12, including the step of selecting a percentage of the incisal to cover a body of the tooth prosthesis.

14. The method of claim 13, including the step of preparing a drawing for the tooth prosthesis to show additional tooth characterization features.

15. The method of claim 14, wherein the step of selecting a brown stain characteristic includes the step of selecting from a plurality of posterior tooth samples having differing brown stain characteristics.

16. The method of claim 15, wherein the step of selecting a white stain characteristic includes the step of selecting from a plurality of posterior tooth samples having differing white stain characteristics.

17. The method of claim 16, wherein the step of selecting an incisal layer color includes the step of selecting from a plurality of posterior tooth samples having differing incisal layer colors.

18. The method of claim 17, wherein the step of selecting a percentage of the incisal to cover the body of the tooth prosthesis, includes the step of selecting from a plurality of posterior tooth samples having differing percentages of the incisal to cover a body of the tooth prosthesis.

19. A method for selecting characterizations for a tooth prosthesis, comprising the steps of:
    selecting a general tooth color for the tooth prosthesis from a shade guide;
    selecting a brown stain characteristic for the tooth prosthesis from an occlusal table, wherein said step further comprises the step of selecting from a plurality of posterior tooth samples having differing brown stain characteristics;

selecting a white stain characteristic for the tooth prosthesis from the occlusal table, wherein said step includes the step of selecting from a plurality of posterior tooth samples having differing white stain characteristics;

selecting an incisal layer color for the tooth prosthesis as an occlusal overlay, wherein said step includes the step of selecting from a plurality of posterior tooth samples having differing incisal layer colors;

selecting a percentage of the incisal to cover a body of the tooth prosthesis, said step including the step of selecting from a plurality of posterior tooth samples having differing percentages of the incisal that covers the body of the tooth prosthesis; and selecting a specific brown stain color for the tooth prosthesis.

20. The method of claim 19, including the step of preparing a drawing for the tooth prosthesis to show additional tooth characterization features.

21. A posterior tooth shade guide for selecting characterizations for a tooth prosthesis, comprising:

means for selecting a brown stain characteristic for the tooth prosthesis from an occlusal table;

means for the tooth prosthesis for selecting a white stain characteristic for the tooth prosthesis from the occlusal table; and means for selecting an incisal layer color for the tooth prosthesis as an occlusal overlay.

22. The posterior tooth shade guide of claim 21, wherein the means for selecting a brown stain characteristic includes a plurality of posterior tooth samples having differing brown stain characteristics.

23. The posterior tooth shade guide of claim 21, wherein the means for selecting a white stain characteristic includes a plurality of posterior tooth samples having differing white stain characteristics.

24. The posterior tooth shade guide of claim 21, wherein the means for selecting an incisal layer color includes a plurality of posterior tooth samples having differing incisal layer colors.

25. The posterior tooth shade guide of claim 24, including means for selecting the percentage of the incisal to cover a body of the tooth prosthesis.

26. The posterior tooth shade guide of claim 25, wherein the means for selecting the percentage of the incisal to cover the body of the tooth prosthesis includes a plurality of posterior tooth samples having differing percentages of the incisal that covers the body of the tooth prosthesis.

27. The posterior tooth shade guide of claim 21, including means for selecting a specific stain color for the tooth prosthesis from a selector ring.

28. The posterior tooth shade guide of claim 27, wherein the selector ring comprises a plurality of sticks pivotally secured to a circular ring, wherein each stick bears a unique brown stain or other color relative to the other sticks secured to the ring.

29. A posterior tooth shade guide for selecting characterizations for a tooth prosthesis, comprising:

a plurality of posterior tooth samples having differing brown stain characteristics;

a plurality of posterior tooth samples having differing white stain characteristics;

a plurality of posterior tooth samples having differing incisal layer colors;

a plurality of posterior tooth samples having differing percentages of the incisal that covers the body of the tooth prosthesis; and a posterior tooth holder having means at an end thereof for holding one of the posterior tooth samples thereon.

30. The posterior tooth shade guide of claim 29, including means for selecting a specific stain color for the tooth prosthesis from a selector ring, the selector ring including a plurality of sticks pivotally secured to a circular ring, wherein each stick bears a unique brown stain or other color relative to the other sticks secured to the ring.

* * * * *